United States Patent
Volker

(10) Patent No.: US 7,610,822 B2
(45) Date of Patent: Nov. 3, 2009

(54) METHOD AND APPARATUS FOR OBTAINING INFORMATION ABOUT THE SIZE DISTRIBUTION OF MACROSCOPIC PARTICLES IN A LIQUID

(75) Inventor: Arno Willem Frederik Volker, Delft (NL)

(73) Assignee: Nederlandse Organisatie voor toegepast-natuurwetenschappelijk Onderzoek TNO, Delft (NL)

(*) Notice: Subject to any disclaimer, the term of this patent is extended or adjusted under 35 U.S.C. 154(b) by 444 days.

(21) Appl. No.: 10/582,282

(22) PCT Filed: Dec. 9, 2004

(86) PCT No.: PCT/NL2004/000857
§ 371 (c)(1), (2), (4) Date: Jun. 9, 2006

(87) PCT Pub. No.: WO2005/057183
PCT Pub. Date: Jun. 23, 2005

(65) Prior Publication Data
US 2007/0091301 A1   Apr. 26, 2007

(30) Foreign Application Priority Data
Dec. 10, 2003   (NL)   .................................. 1024984

(51) Int. Cl.
*G01N 15/00* (2006.01)

(52) U.S. Cl. ..................................................... 73/865.5
(58) Field of Classification Search .................. None
See application file for complete search history.

(56) References Cited

U.S. PATENT DOCUMENTS
3,779,070 A   12/1973   Cushman et al.

FOREIGN PATENT DOCUMENTS
EP          0989397 A      3/2000
WO      WO 03/102550 A   12/2003

OTHER PUBLICATIONS
International Search Report.

*Primary Examiner*—Robert R Raevis
(74) *Attorney, Agent, or Firm*—Leydig, Voit & Mayer Ltd.

(57) ABSTRACT

On the basis of a series of reflection measurements on a liquid, parameters are calculated which describe a particle size distribution of particles in the liquid. In each reflection measurement, a signal beam is generated in the liquid and a value of a property such as the amplitude of a reflection on a particle in the signal beam is measured. Using maximum likelihood estimation, the parameters of the particle size distribution are estimated, on the basis of an expression for a probability of the measured values as a function of the measured values. The expression used contains a first factor for the probability of a reflection measurement of which a reflection with the measured value forms part, corrected with a second factor for the probability that there is not also a reflection with a dominating value of the property, which would mask the measured values, forming part of the reflection measurement.

10 Claims, 5 Drawing Sheets

METHOD AND APPARATUS FOR OBTAINING INFORMATION ABOUT THE SIZE DISTRIBUTION OF MACROSCOPIC PARTICLES IN A LIQUID

FIELD OF THE INVENTION

The invention relates to a method and apparatus in which, using reflection of ultrasonic pulses by macroscopic particles such as oil droplets or sand grains in water, information about the size distribution of the particles in a liquid is determined.

BACKGROUND

European patent application No. 0801305 describes an apparatus for characterizing a suspension. The apparatus generates ultrasonic pulses in a beam in a liquid. Reflection of a pulse on an individual particle in the liquid results in an echo. If the particle is at a given position, the amplitude of the reflection is coupled one-to-one to the size of the particle. Accordingly, in measurements on reflections of consecutive pulses on particles of different sizes, different amplitudes are measured.

The known apparatus makes a histogram of counts of the number of times that reflections of different amplitudes occur. The histogram contains information about the particle size distribution, that is, the concentration of particles as a function of the size of the particles. With information about the particle size distribution, in turn, for instance the total concentration of particles in the liquid can be determined.

European patent application No. 0801305 describes a technique to extract information about the size from the distribution of the amplitudes. An expression is used for the probability that reflections of different amplitudes occur. This expression relates the probability to the particle size distribution. If the reflecting particles were always at the same place in the beam, the number of reflections having a particular amplitude would be proportional to the fraction of particles having the size leading to that amplitude.

However, the information about the particle size distribution is smeared across the amplitudes because the reflection amplitude of a particle, besides being dependent on the size of the particle, also depends on the position of the particle in the beam. The farther the particle is off the center of the beam at reflection, the smaller the amplitude. The expression used for the probability of a reflection measurement with a particular amplitude smears the particle size distribution across the amplitude distribution to give expression to this effect.

Using a maximum likelihood technique, parameters of the particle size distribution are estimated that maximize the thus expressed probability of the actually measured numbers of particles. Thus, smearing is undone. In the concrete, the parameters are chosen such that a sum is minimized of the squares of the differences between measured numbers of reflections with amplitudes in different amplitude ranges and predicted numbers. Such a sum is an indication for the probability of the combination of measured reflections, but of course also other indications of the probability can be used, such as the product of the probabilities of the different measured amplitudes.

A prerequisite for the technique used is that the reflections of individual particles can be distinguished. If reflections of several particles are measured indiscriminately, a part of the reflections will be masked. Thus, reflection of a larger particle can make reflection of a smaller particle invisible, but reflection of a smaller particle can also mask reflection of a larger particle if the larger particle is sufficiently much farther from the center of the beam than is the smaller particle.

Accordingly, the technique gives reliable results only when concentrations are sufficiently low. The maximum usable concentration can be raised by minimizing the volume in which particles are indistinguishably measured, for instance by the use of a focused beam and small time windows in which echoes are accepted. However, there are limits to the applicability of such techniques. That is why the requirement of separate observation of individual particles limits the applicability of the technique.

SUMMARY OF THE INVENTION

It is an object of the invention to make the use of ultrasonic measurements for the characterization of particle size distribution in liquids useful for higher concentrations.

The present invention is based on the realization that it is possible with a statistical model to correct for the effect of particles being missed and that consequently the known measuring technique can also be used for larger concentrations.

The invention provides a method according to claim 1. In the method, the parameters of the particle size distribution are estimated with a maximum likelihood technique, using an expression for the probability of measurement of reflection amplitudes in terms of two factors. The first factor expresses the probability $P_o(A)$ of a reflection measurement of which a reflection with the value A forms part, independently of the question whether this value is masked in that also a reflection with a greater value occurs. This first factor basically corresponds to the whole expression for the probability used in the state of the art.

The second factor in the expression used according to the invention comprises the probability that there is not also a reflection with a dominating value of the property, which would mask the measured value, forming part of the reflection measurement. Thus, the effect of masking is taken into account in the estimation of the parameters. In this way, the maximum likelihood estimation takes into account both the effect of spreading and the effect of masking jointly.

BRIEF DESCRIPTION OF THE DRAWINGS

These and other objects and advantageous aspects of the invention will be described with reference to the following figures.

DETAILED DESCRIPTION OF THE DRAWINGS

Figure 1:
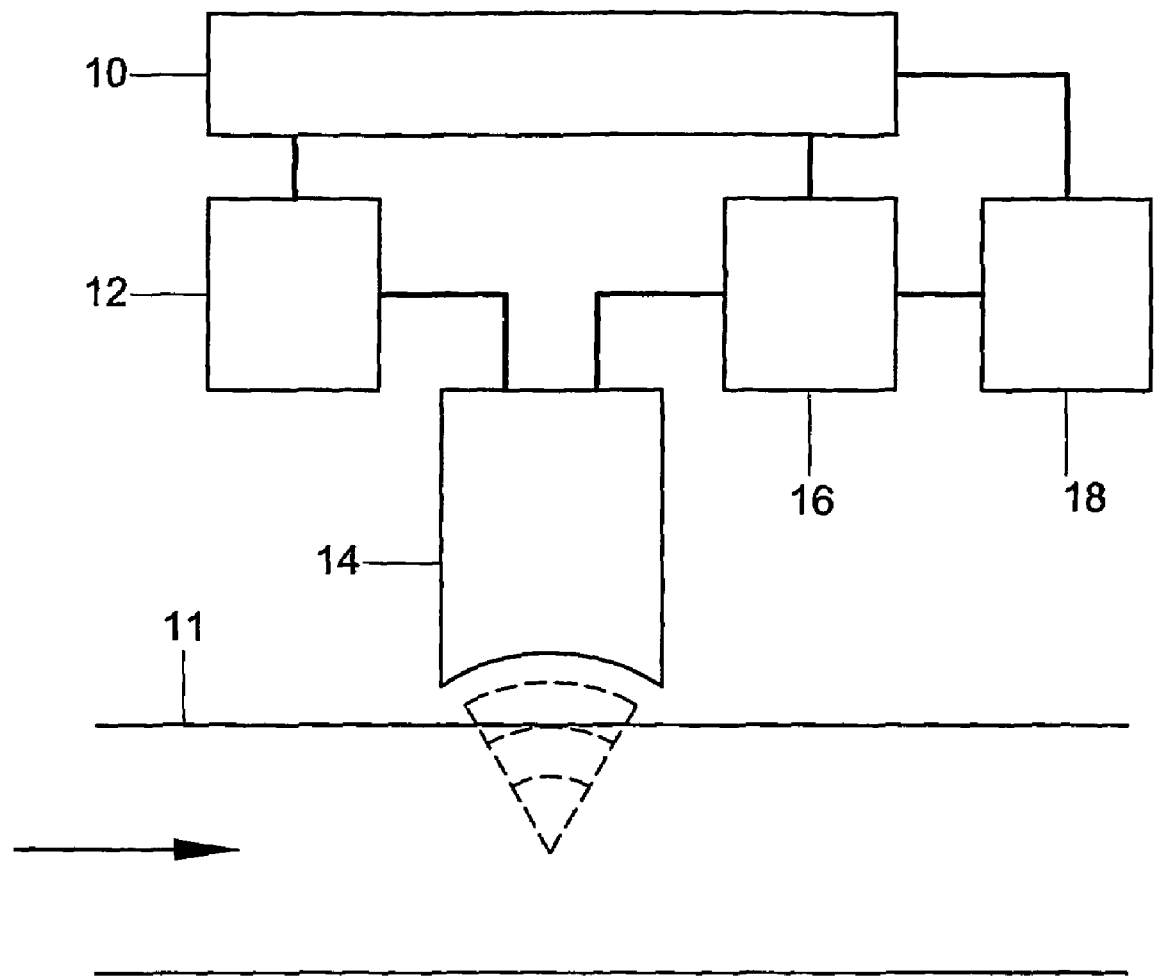
FIG. 1 shows an apparatus for characterizing a liquid

FIG. 1 shows an apparatus for characterizing a liquid. The apparatus comprises a liquid channel 11, a control unit 10, a signal generator 12, an ultrasonic transducer 14, a detector 16 and a calculating unit 18. Control unit 10 is coupled to signal generator 12, detector 16 and calculating unit 18. Signal generator 12 has an output coupled to transducer 14. Detector 16 has an input coupled to transducer 14. Detector 16 has an output coupled to calculating unit 18. Transducer 14 is coupled to channel 11 for generating an ultrasonic beam.

In operation, a liquid with particles floating therein flows through channel 11. Control unit 10 triggers consecutive reflection measurements in each of which signal generator 12 generates a pulse which is converted by transducer 14 to an ultrasonic wave in channel 11. Transducer 14 captures reflections of the pulse and feeds resulting signals to detector 16. Detector 16 selects signals which occur in a particular time window with respect to the generated pulse. As a result of the sound velocity in liquid, the time window defines a zone from where particles can give rise to reflections. Detector 16 measures the amplitude of the reflection signal (if present) in the time window and feeds the measured value of the amplitude to calculating unit 18. Calculating unit 18 collects histogram information of the amplitudes. To that end, the calculating unit utilizes a number of amplitude ranges and cumulates counts of the number of reflection measurements that have yielded reflection amplitudes in the respective ranges. After a large number of reflection measurements have thus been performed, calculating unit 18 calculates further information about the particle size distribution from the histogram information.

Figure 2:
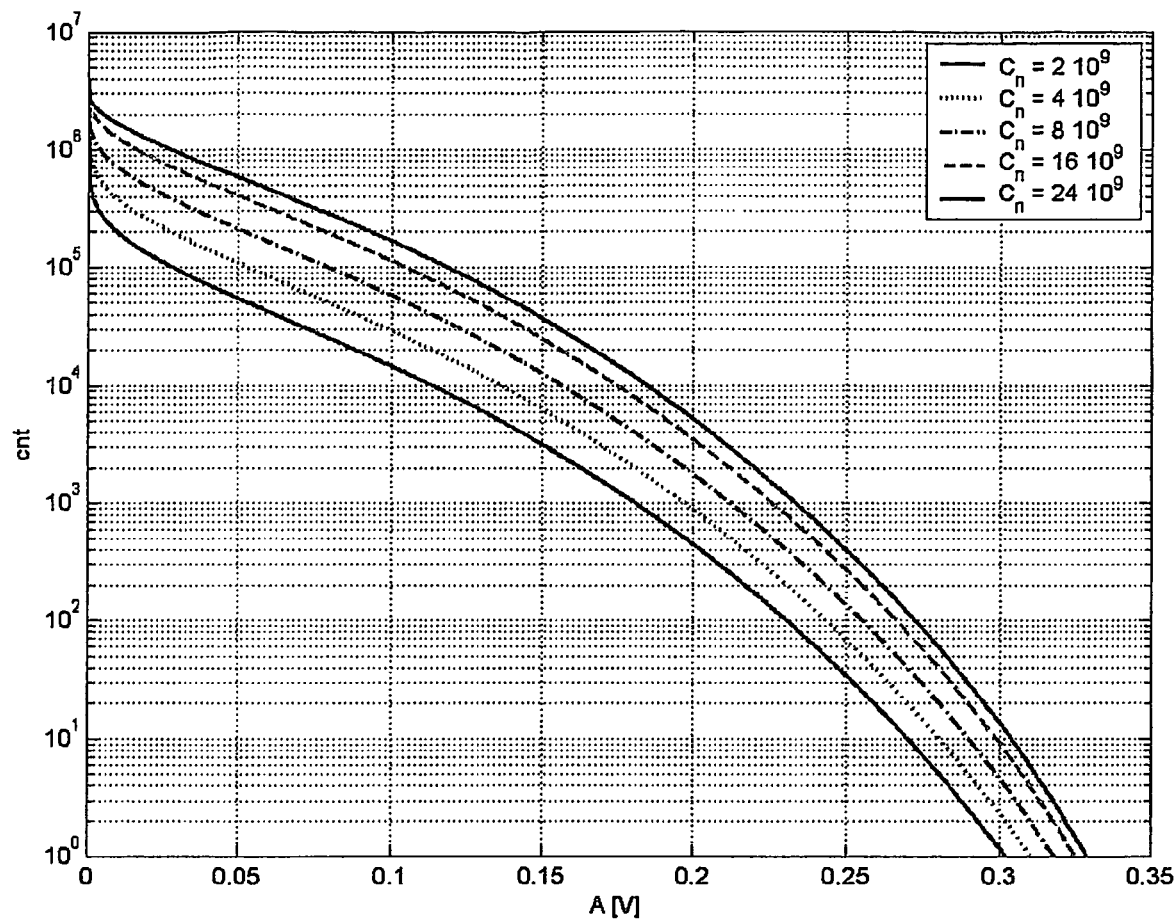
FIG. 2 shows numbers of reflections with different amplitudes

FIG. 2 shows a simulated example of histograms for liquids in which different concentrations of particle are present, while the particle size distribution $f_D(D)$ in each case is the same (that is, the fraction of the particles having a size between D and D+dD in each case is $f_D(D)dD$ for each value of D). It can be seen that, besides an increase of the numbers of reflections, also the shape of the amplitude distribution changes with increasing concentration.

Figure 3:
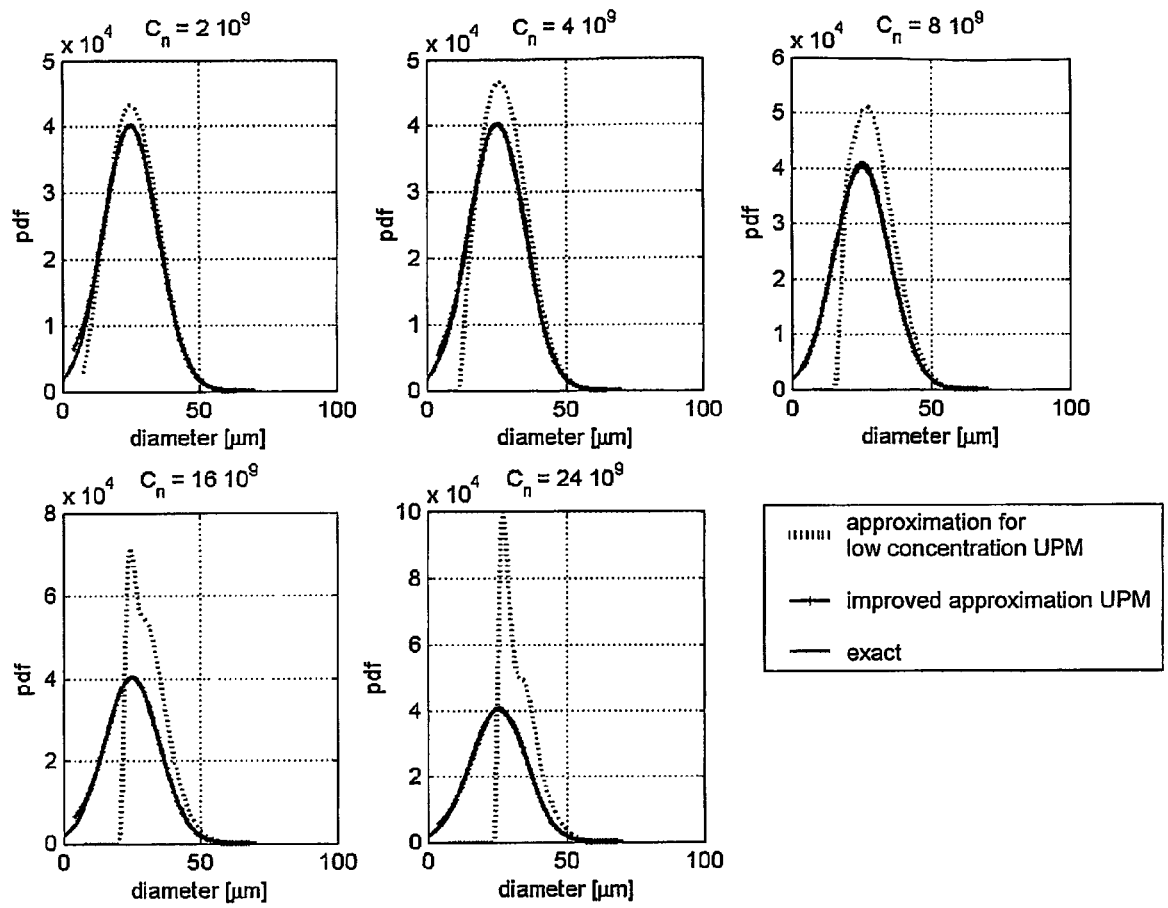
FIG. 3 shows a reconstructed particle size distribution

FIG. 3 shows, in dotted lines, estimates of the particle size distribution that can be calculated from the amplitude histograms on the basis of the known technique, for a number of different concentrations. Also shown is the true distribution. The known technique does not take into account the effect of the concentration on the shape of the amplitude distribution. The result is that the estimated particle size distributions are mutually different and at higher concentrations deviate from the true particle size distribution.

The invention provides an improvement of the known technique of estimating the particle size distribution, so that the effect of the concentration of the particles can be corrected for as well. This improvement is based on the realization that the deviation of the shape of the histograms of FIG. 2 is a result of masking of reflection amplitudes which occur in the reflection measurement but are missed in the count because in the same reflection measurement one or more reflections with a greater amplitude occur.

To that end, an expression is used for the probability distribution P(A)dA that a reflection measurement yields a measured amplitude which is in an infinitesimal interval between A and A+dA. This expression is in the form of $$P(A) = P_o(A) \, Q(A)$$

Herein, $P_o(A)$ corresponds to the unmasked probability distribution, that is, probability of presence of a reflection, regardless of the question whether it is masked by another reflection having a greater amplitude. The factor $Q(A)$ expresses the probability that in the same reflection measurement no particles cause reflections of an amplitude greater than or equal to A.

The factor $P_o(A)$ corresponds to the probability distribution that is used in the state of the art for the whole probability distribution P(A) that an amplitude A in the interval A to A+dA is in fact measured (i.e. with neglect of the possibility that a reflection is masked). This factor $P_o(A)$ can be expressed in the particle size distribution $f_D(D)$ in a manner known per se. An expression for this factor is, for instance, $$P_o(A) = C \int dD \, f_D(D) G(A|D) V_{meas}(D)$$

Herein, C is the concentration of the particles (the average number of particles per unit volume). G(A|D) is the conditional probability that a reflection of amplitude A is detectable, if a particle of a size D yields a detectable reflection. The conditional probability G(A|D) expresses the effect that a particle of a size D gives rise to different reflection amplitudes at different distances from the center of the beam. $V_{meas}(D)$ is the total volume of liquid from where a particle of size D can yield a detectable reflection. This volume is defined in depth by the time window from where reflections are accepted during the measurement and laterally by the decay of the beam intensity to a point where the amplitude of the generated reflections no longer projects above the noise level $A_n$.

In the frequently occurring case of a Gaussian distributed beam, the volume $V_{meas}(D)$ can be expressed as $$V_{meas}(D) = \pi \Delta z \, \log(A_o(D)/A_n)/2\kappa$$

Herein, $\Delta z$ is the depth interval from where reflections are accepted, $\kappa$ is the standard deviation which is determined by the rate at which the intensity of the beam decays as a function of the distance to the center of the beam. $A_o(D)$ is the maximum amplitude that a reflection of a particle of size D would yield if the particle were located in the center of the beam.

For a Gaussian beam, also an expression for the conditional probability G(A|D) can be given:

$$G(A|D) = 1/\{A * \log(A_o(D)/A_n)\}$$

This expression applies provided that $A_o(D) > A > A_n$. For amplitudes greater than the maximum amplitude $A_o(D)$ attainable with a particle size D, or smaller than the noise level $A_n$, the conditional odds of detection G(A|D) equal zero.

It will be clear, incidentally, that for beams having a distribution other than Gaussian, correspondingly different expressions for $V_{meas}(D)$ and G(A|D) will be used.

The newly introduced factor Q(A), which expresses the effect of reflections being masked by other reflections having an amplitude greater than or equal to the amplitude A, can also be expressed in terms of the concentration C and the particle size distribution $f_D(D)$. Normative for this is the integral expression $$W(A) = \int dA' \int dD \, f_D(D) G(A'|D)$$

Herein, the integral over the amplitude is taken from the noise level up to the amplitude A, for which the odds of detection are being calculated. The factor Q can be approximated by $$Q(A) = \exp[-C(1 - W(A))]$$

Or, in approximation, by a factor $$Q(A) = [1 - p + p(1 - W(A)/V_{meas})]^n$$

wherein the sum over k is taken from 1 to n; n is an integer not greater than the maximum number of particles that physically fit into the volume from where measurable reflections occur, but amply greater than the average number of particles that yield measurable reflections and p=CVmeas/n, where Vmeas is the volume from where the largest particles can still generate echoes above the noise level.

An alternative expression for the $P_o(A)$ factor is for instance $$P_o(A) = C \int dD \, f_D(D) \, \partial V(A,D)/\partial A$$

Herein, C is the concentration of the particles (the average number of particles per unit volume). V(A,D) is the volume from where a particle of size D yields an echo of an amplitude greater than or equal to A. This volume is defined in depth by the time window from where reflections are accepted during the measurement and laterally by the decay of the beam intensity with the distance to the center of the beam.

In the frequently occurring case of a Gaussian distributed beam, the volume V(A,D) can be expressed as $$V(A, D) = \pi \Delta z \log(Ao(D)/A)/2\kappa$$

Herein, $\Delta z$ is the depth interval from where reflections are accepted, $\kappa$ is a parameter which characterizes the rate at which the intensity of the beam decays as a function of the distance to the center of the beam. Ao(D) is the maximum amplitude that a reflection of a particle of size D would yield if the particle were located in the center of the beam. It will be clear, incidentally, that for beams having a distribution other than Gaussian, correspondingly different expressions for V(A, D) will be used.

The newly introduced factor Q(A) expresses the probability that besides the echo of amplitude A no echoes of greater amplitude occur. This describes the effect of reflections being masked by other reflections of an amplitude greater than or equal to the amplitude A. The factor Q(A) can also be expressed in terms of the concentration C and the particle size distribution $f_D(D)$). Normative for this is the integral expression $$W(A) = \int dD \, f_D(D) V(A,D)$$

The factor Q can be approximated by $$Q(A) = \exp[-CW(A)]$$

On the basis of the expression $P(A) = P_o(A) \, Q$ for the probability distribution of measurements of reflections of amplitude A that are not masked by reflections of greater amplitude, the particle size distribution $f_D(D)$ is estimated from the system of reflection amplitudes that has been measured in a large number of measurements. This is done, for instance, by looking for an estimate $f_D(D)$ which minimizes the sum E of the squares of differences between the predicted numbers of measurements $N_{pred}$ of amplitudes in a series of amplitude intervals $IA_i$ and the actually measured numbers $N_{meas}$ $$E = \Sigma_i \, (N_{meas}(IA_i) - N_{pred}(IA_i))^2$$

This sum is in fact an indication for the probability of the measured system of amplitudes, so that the particle size distribution $f_D(D)$ is chosen that makes this system most probable. Of course, instead of using the sum of the squares, maximization can also be done using other indications of the probability, for instance using a product $$\Pi_i P_o(A_i) \, Q(A_i)$$

of the probabilities of the different measurements $A_i$.

In this estimation, preferably a parameterization of the particle size distribution $f_D(D)$ is used, for instance in the form of a multimodal distribution $$f_D(D) = \Sigma_i \, c_i \exp(-(D-D_i)^2/2\sigma_i^2)$$

(i=1, 2 ... M). In this case, the parameters $c_i$, $D_i$ and $\sigma_i^2$ are estimated such that according to the indication used, the probability of the measured system of reflection amplitudes is maximized. Techniques for such maximizations are known in general, and by applying them to an expression $P_o(A) \, Q(A)$ for the probability of measured (and not masked) reflection amplitudes, an estimate for the parameters is obtained.

FIG. 3 further shows different particle size distributions which are thus calculated from the numbers of reflections in the examples of FIG. 2. These distributions virtually coincide, within the accuracy of the figure, with the true distribution. It will be clear that thus a better estimate of the particle size distribution is obtained.

Figure 4:
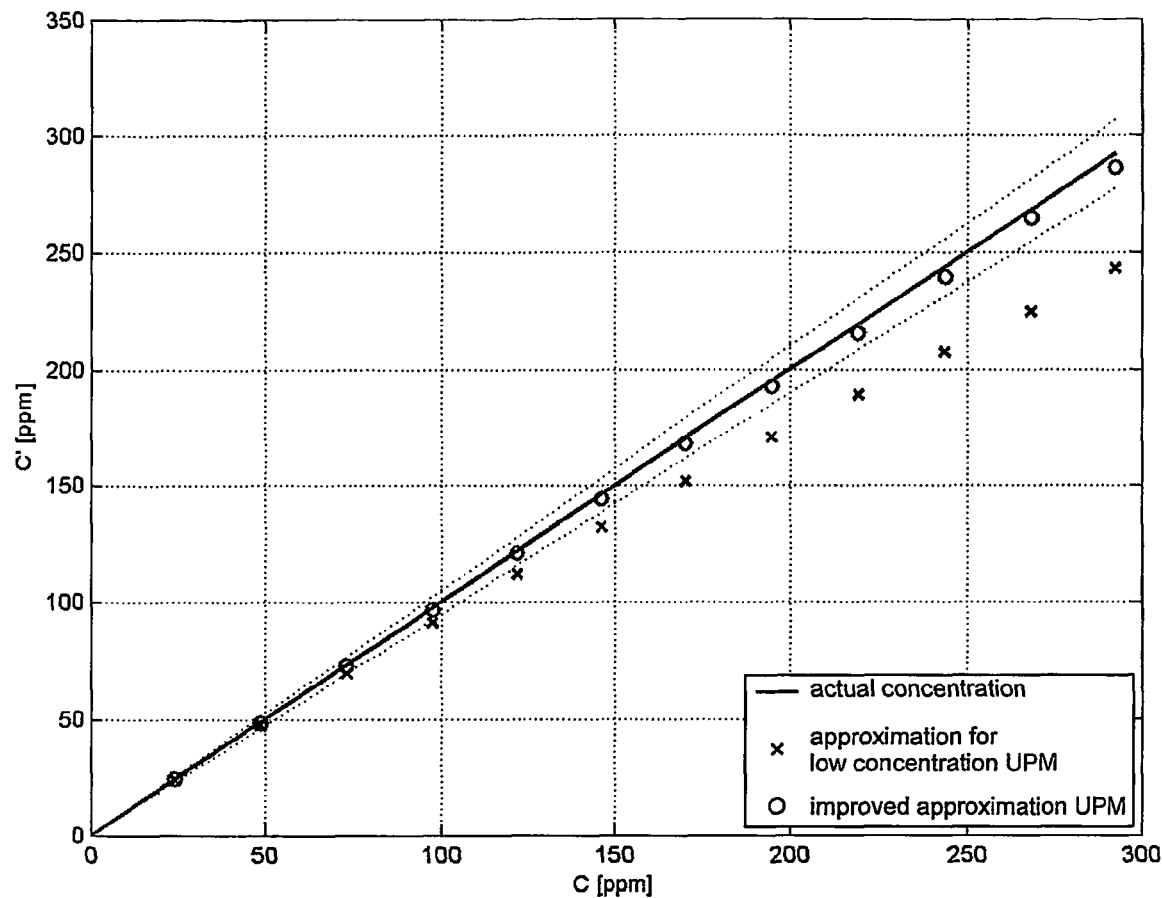
FIG. 4 shows a calculated concentration

FIG. 4 shows the consequences of the estimate of the particle size distribution for the concentration. The concentration is the fraction of the liquid that is formed by the particles. Plotted horizontally is the true concentration and plotted vertically is the concentration calculated from the (simulated) measurements. The solid line indicates where calculated and true concentration are equal. The circles indicate the concentration calculated with the new technique and the crosses indicate the concentration calculated with the state of the art. The figure shows that especially for higher concentrations clearly better results are obtained.

It will be clear that the invention is not bound to this specific manner of estimating the particle size distribution. Thus, for instance, a different form of parameterizing the particle size distribution can be used, for instance on the basis of the values (and/or derivatives) of the particle size distribution for a number of particle sizes and an interpolation of the particle size distribution between these particle sizes, or, for instance, in the form of a quotient of two polynomials, whose coefficients form the parameters. Also, approximations for the different terms in the mathematical formula for the probability P(IA) can be used.

Further, for instance, first an estimate can be made of the factor Q(A) as a function of the amplitude A (for instance by provisionally estimating the particle size distribution and subsequently calculating the factor with that provisionally estimated distribution), and then the measured numbers of reflections $N_{meas}(A)$ with different amplitudes can be corrected with this factor $N_{corr}(A) = N_{meas}(A)/Q(A)$. Next, from the corrected numbers, the particle size distribution can be estimated in the manner known from the state of the art.

Although the invention has been described in terms of the explicit particle size distribution $f_D(D)$, it will be clear that for certain applications it is not necessary to actually calculate this particle size distribution explicitly. When only a quantity such as for instance the mass density of particles is needed, which follows from the integral $$\int dD \, f_D(D) \, m(D)$$

then this quantity, which is a parameter of the particle size distribution, can also be calculated implicitly when estimating the parameters of the particle size distribution that makes the system of measured reflection amplitudes the most probable.

The technique used is not limited to measurements on amplitudes, but can be extended to any form of measurements of properties of the reflections whereby, in the presence of more particles causing reflections, the effect of a dominating particle masks the effect of the other particles.

The technique is especially also applicable to liquids that contain different types of particles, when a distinction can be made as to which type of particle gives rise to a reflection measurement. This distinction may for instance be visible on the reflection signal itself, for instance by the sign of the first peak in a received ultrasonic reflection signal in response to an ultrasonic pulse of a particular sign. In the case of water in which oil droplets and sand grains are dissolved, for instance, reflections on sand grains and oil droplets can be distinguished by the sign of the reflection.

The corrected probability distribution $P_j(A)dA$ for a measurement of a reflection of a particle of type j, with an amplitude in a range between A and A+dA, can in this case be described with $$P_j(A) = P_{jo}(A) \Pi_i Q_i(A)$$

Herein, different factors $Q_i(A)$ describe for each different type of particles i the probability that no particles of the type i lead to detection with greater amplitude than A. The factors $Q_i(A)$ are each expressed in the above-described manner in the particle size distribution $f_{D,i}(D)$ of a respective type of particles i, and so are the probabilities $P_{jo}(A)$. With these expressions for $P_j(A)$ for different types of particles and a system of measurements of reflection amplitudes that are classified according to the type of particles involved, parameters of the particle size distributions $f_{Di}(D)$ can be estimated in the above-described manner. Thus, for instance, particle size distributions can be estimated which minimize a composite sum of squares of deviations $$E = \Sigma_i \Sigma_m (Ni_{meas}(IA_m) - Ni_{pred}(IA_m))^2$$

of the numbers $Ni_{meas}$ of measured reflections of particles of type m in different amplitude ranges $IA_m$ and the predicted numbers $Ni_{pred}$ of measured reflections in these ranges.

Figure 5:
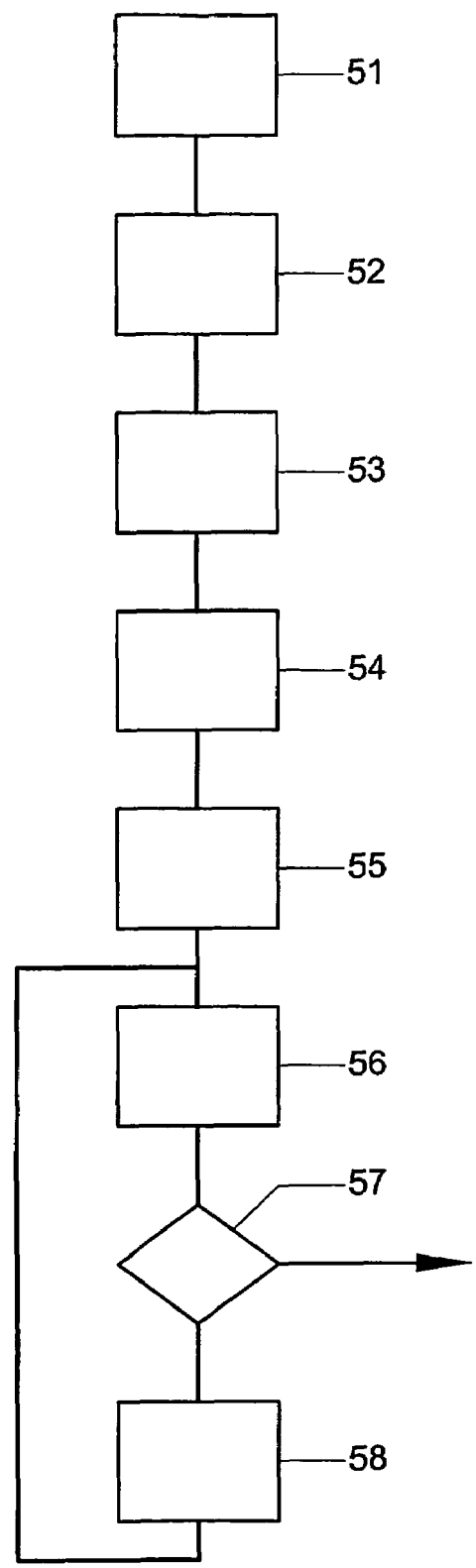
FIG. 5 shows a flow chart of a method of estimating parameters of a particle size distribution.

FIG. 5 shows in summary the method for estimating the particle size distribution. In a first step 51, a pulse is generated and in a second step 52 it is detected whether in a particular time window after the pulse a reflection above the noise level returns. In a third step 53 it is determined in which of a number of intervals IA the amplitude falls and in a memory a count for the interval in question is increased. From a fourth step 54, the previous steps are repeated until a particular number N of reflection experiments have been performed. Next, a fifth step 55 is performed in which parameters of an initial particle size distribution are chosen. With these, in a sixth step 56, using the formula $P(A) = P_o(A) Q(A)$, a prediction of the measured numbers is calculated and a difference with the measured numbers is determined. If the difference is sufficiently small, the method stops in a seventh step 57. If not, in an eighth step 58, the parameters are adjusted such that the difference will expectably decrease, and the method is repeated from the sixth step 56. Of course, estimation in the method is preferably carried out with a computer.

It will be clear that the invention is not limited to the method described. For instance, in the sixth step 56, the difference does not need to be calculated explicitly, but instead information can be calculated that is needed to choose the adjustment of the parameters, and the method can stop in the seventh step 57 if the adjustment is less than a threshold.

The invention claimed is:

1. A method for measuring parameters which describe a particle size distribution of particles in a liquid, which method comprises the steps of:
   performing a series of particle reflection measurements, in each of which a signal beam is generated in the liquid and a measured value (A) of a property of a reflection of the signal beam by a particle in a path of the signal beam in the liquid is measured;
   performing a maximum likelihood estimation of the parameters in view of a combination of the measured values (A), based on an expression for a probability of the measured values as a function of the measured values, which expression contains a first factor (P) for a probability of a particle reflection measurement of which a reflection with the measured value forms a part, corrected with a second factor (Q) for a probability that there is not also a particle reflection in the liquid with a dominating value of the property, which would mask the measured value, forming part of the particle reflection measurement.

2. A method according to claim 1, wherein the first factor (P) comprises the particle size distribution, smeared with a probability distribution that a particle in the liquid of a particular size leads to a particle reflection measurement of which a particle reflection with the measured value forms a part.

3. A method according to claim 2, wherein the second factor (Q) comprises a probability that a particle reflection with a value other than the measured value forms part of a particle reflection measurement, integrated over a range of values other than the measured values.

4. A method according to claim 3, wherein the second factor substantially corresponds to $\exp(-C \int dA' \int dD\, f_D(D) G(A'|D))$, wherein D is a particle size, C is a concentration of the particles, $f_D(D)$ is a density of particles of particle size D, and $G(A|D)$ is a conditional probability that a reflection by a particle in the liquid with amplitude A is detectable, if a particle of a size D yields a detectable reflection.

5. A method according to claim 1, wherein the second factor (Q) comprises a probability that a particle reflection in the liquid with a value other than the measured value forms part of a particle reflection measurement, integrated over a range of values other than the measured values.

6. A method according to claim 5, wherein the second factor substantially corresponds to $\exp(-C \int dA' \int dD\, f_D(D) G(A'|D))$, wherein D is a particle size, C is a concentration of the particles, $f_D(D)$ is a density of particles of particle size D, and $G(A|D)$ is a conditional probability that a reflection by a particle in the liquid with amplitude A is detectable, if a particle of a size D yields a detectable reflection.

7. A method according to claim 1, wherein the maximum likelihood estimation step comprises performing counts of numbers of reflection, measurements in which the measured values fall into respective value intervals, and an estimate is chosen such that a complex of deviations between counts in the different intervals and counts predicted according to a probability as a function of the measured values is minimized.

8. A method according to claim 1, wherein in the particle reflection measurements a distinction is made between different types of particles in the liquid that cause reflections, and in performing the maximum likelihood estimation step the expression is corrected with a product of respective second factors for the probability that there is not also a particle reflection in the liquid with a dominating value of the property by respective types of particles, which would mask the measured value, forming part of the particle reflection measurement.

9. An apparatus for measuring parameters which describe a particle size distribution of particles in a liquid, which apparatus comprises:
   a liquid channel;
   an ultrasonic transducer assembly for generating an ultrasonic beam in the liquid channel containing the liquid;
   a detector for measuring a property of a reflection of the beam by a particle in the liquid in the liquid channel to provide a signal corresponding to a measured value;
   a processing unit arranged for performing a maximum likelihood estimation of the parameters, in view of a combination of a series of the measured values, based on an expression for a probability of the measured values as a function of the measured values, which expression contains a first factor for a probability of a particle reflection measurement of which a particle reflection with the measured value forms part, corrected with a second factor for a probability that there is not also a reflection by a particle in the liquid with a dominating value of the property, which would mask the measured value, forming part of the particle reflection measurement.

10. A computer program product with instructions for measuring parameters which describe a particle size distribution of particles in a liquid, based on a series of particle reflection measurements, in each of which a signal beam is generated in the liquid and a measured value (A) of a property of a reflection by a particle in a path of the signal beam in the liquid is measured; and wherein the instructions are arranged for performing the steps of:

generating a maximum likelihood estimation of the parameters in view of a combination of the measured values (A), on the basis of an expression for a probability of the measured values as a function of the measured values, which expression contains a first factor (P) for a probability of a particle reflection measurement of which a particle reflection with the measured value forms a part, corrected with a second factor (Q) for a probability that there is not also a particle reflection with a dominating value of the property, which would mask the measured value, forming part of the particle reflection measurement.

* * * * *

UNITED STATES PATENT AND TRADEMARK OFFICE
CERTIFICATE OF CORRECTION

PATENT NO. : 7,610,822 B2 Page 1 of 1
APPLICATION NO. : 10/582282
DATED : November 3, 2009
INVENTOR(S) : Arno Willem Frederik Volker It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 588 days.

Signed and Sealed this

Twelfth Day of October, 2010

David J. Kappos
*Director of the United States Patent and Trademark Office*